United States Patent [19]

Peers-Travarton

[11] Patent Number: 4,667,686
[45] Date of Patent: May 26, 1987

[54] PACER LEAD TERMINAL ASSEMBLY

[75] Inventor: Charles A. Peers-Travarton, Pompano Beach, Fla.

[73] Assignee: Cordis Corporation, Miami, Fla.

[21] Appl. No.: 734,657

[22] Filed: May 16, 1985

[51] Int. Cl.$^4$ ............................................. A61N 1/04
[52] U.S. Cl. ................................ 128/785; 128/419 P
[58] Field of Search .................... 128/419 P, 784–786; 339/5, 6, 8

[56] References Cited

U.S. PATENT DOCUMENTS

| | | | |
|---|---|---|---|
| 2,119,168 | 5/1938 | Kus | 339/8 PB |
| 2,473,705 | 6/1949 | George | 339/5 S |
| 3,017,595 | 1/1962 | Drollinger et al. | 339/8 P |
| 3,441,765 | 4/1969 | Maybury et al. | 339/5 S |
| 4,381,013 | 4/1983 | Dutcher | 128/786 |
| 4,463,765 | 8/1984 | Gold | 128/785 |
| 4,570,642 | 2/1986 | Kane et al. | 128/419 P |
| 4,577,643 | 3/1986 | Beranek | 128/419 P |

Primary Examiner—William E. Kamm
Attorney, Agent, or Firm—George H. Gerstman

[57] ABSTRACT

An active fixation lead comprises a length of insulated electrical wire having a rotatable terminal pin at one end thereof. Driver coil means are connected to the terminal pin and extend within the lead to the other end of the lead. Fixation means are carried at the other end of the lead having an affixing position and a retracted, non-affixing position. The fixation means are connected to the driver coil means and movable between positions by rotation of the terminal pin. By this invention a first conductive metal sleeve adjacent the one end of the lead is provided, with the first sleeve being electrically connected to the electrical wire. A second conductive metal sleeve is electrically connected to the terminal pin. The first and second sleeves are secured together in telescoping relation with the second sleeve being rotatable. A conductive metal strip of gold or the like is positioned between the first and second sleeves. Accordingly, improved electrical contact is provided between the terminal pin and the electrical wire.

4 Claims, 4 Drawing Figures

PACER LEAD TERMINAL ASSEMBLY

BACKGROUND OF THE INVENTION

In Dutcher U.S. Pat. No. 4,217,913 and Gold U.S. Pat. No. 4,463,765 body implantable leads particularly for carrying electrical impulses to stimulate and regulate the heart muscle are disclosed. The specific leads each define fixation means which comprises an initially retracted, advanceable corkscrew pin which, after positioning of a forward electrode on the lead in the desired position, may be advanced into the tissue of the heart, or other tissue as desired, to retain the electrode and its lead in the appropriate position.

The fixation means is advanced and retracted by a drive mechanism which includes driver coil means extending the length of the lead and connected at the outer or proximal end of the lead assembly to the terminal pin. Thus, the terminal pin provides the double function of being capable of connection to the source of heart muscle-stimulating electrical power, but it also constitutes a handle which can be rotated to advance or retract the fixation means positioned at the other end of the lead.

In the prior designs, problems have been encountered because of the rotatable nature of the terminal pin. In the prior designs, difficulties have arisen in the maintenance of a good electrical connection between the terminal pin and the electrical wire or wires in the lead, with the problem centering on the fact that the terminal pin is rotatably movable with respect to the electrical wire, which tends to be fixed and non-rotatable. Significant electrical resistance can develop in the long term use of a cardiac pacer-lead at the junction between the stationary electrically conductive parts connected to the wire or wires, and the rotatable part or parts connected to the terminal pin. It is of course a matter of great criticality for the lead to maintain an undiminished electrical connection between the terminal pin and the distal electrode within the body, positioned typically against or in the heart. A failure of electrical connection, of course, causes a complete failure of the pacer itself.

By this invention an improved electrical connection is provided between the terminal pin and the electrical wire which communicates with the distal electrode, for increased reliability of active fixation type leads, in which the terminal pin is rotatable for moving the fixation means between its retracted, nonaffixing and its affixing positions

DESCRIPTION OF THE INVENTION

In this invention, an active fixation lead comprises a length of insulated electrical wire having a rotatable terminal pin at one end thereof. Driver coil means are connected to the terminal pin, extending within the lead to the other end of the lead. Fixation means are carried at the other end of the lead, having an affixing position and a retracted, non-affixing position. The fixation means are connected to the driver coil means and movable between its positions by rotation of the terminal pin.

In accordance with this invention, a first conductive metal sleeve is positioned adjacent one end of the lead, with the first sleeve being electrically connected to the electrical wire. A second conductive metal sleeve is electrically connected to the terminal pin. The first and second sleeves are secured together in telescoping relation with the second sleeve being rotatable.

A conductive metal spring strip is positioned between the first and second sleeves. The spring strip is biased out of its natural, unstressed position, so that the strip presses against both the first and second conductive sleeves by spring action. As the result of this, improved electrical contact is provided between the terminal pin and the electrical wire.

The spring strip may be positioned in an annular groove defined in one of the sleeves, being typicailly biased into a "C" or almost "O" shape, although it is preferred for the ends of the spring strip, even when in essentially "O" shape, to be spaced from each other.

The spring strip may assume a substantially flat position, or at least some other position than the "C" or "O" shape, in its natural, unstressed configuration. Accordingly, when forced into a "C" or "O" configuration, the spring strip is biased out of its natural position to press against both the first and second conductive sleeves by spring action. Accordingly, the improved electrical contact between the two sleeves is achieved.

Preferably, the conductive metal spring strip is made of gold, including highly conductive gold alloys.

The second conductive metal sleeve is preferably connected to the terminal pin in screw-threaded relation. The two members may be spot welded together as well, to increase electrical conductivity between them.

The second sleeve may carry a portion of the first sleeve in its bore, with the second sleeve defining inwardly projecting tabs. The first sleeve may then define an upwardly facing annular slot positioned to receive the tabs. The effect of this is to prevent disconnection of the sleeves from their telescoping relation.

At the distal end of the lead, the electrical wire may connect with a sleeve electrode which is positioned adjacent the fixation means. The fixation means may be carried on a shaft which is connected to the driver coil, with the shaft being positioned within sleeve means which may be part of the sleeve electrode.

A sealing skirt member may then be sealed to the shaft to form a resilient, annular, sliding seal with the sleeve means. Accordingly, the sealing skirt provides dynamic sealing as the fixation means is moved between its protracted, non-affixing position and its a fixing position. The fixation means may be a helical pin.

DESCRIPTION OF THE DRAWINGS

In the drawings, FIG. 1 is a partially schematic view of an active fixation lead for use in a cardiac pacer, made in accordance with this invention.

FIG. 2 is a longitudinal sectional view of both ends of the active fixation lead of FIG. 1.

FIG. 3 is an enlarged sectional view taken along line 3—3 of FIG. 2.

FIG. 4 is a sectional view taken along line 4—4 of FIG. 2.

DESCRIPTION OF SPECIFIC EMBODIMENT

Referring to the drawings, cardiac pacing lead 10 includes a distal electrode assembly 12. The lead body 14 comprised coiled lead wire or wires 24 enclosed in tubular insulation 17.

At the opposite end of pacing lead 10 is the pacer lead terminal assembly 16, which may be electrically connected to pulse generator 18 of conventional design, and adapted to convey pulses from generator 18 to helical conductor wire or wires 24. Wire 24, in turn, conveys the electrical impulse to tubular electrode 12 at the distal end of pacing lead 10.

Insulating sheath 17 may be made of silicone rubber, polyurethane, or any other desired inert, physiologically compatible plastic material to protect the interior of the pacing lead. Sheath 17 may have annular ridges 32, which serve as protective seals when the proximal end of lead 10 including terminal assembly 16 is inserted into a cardiac pacer of known design for receiving electrical pulses from pulse generator 18.

Stylet 20 may pass through central bore or aperrure 21, which extends substantially the length of pacer lead 10 to facilitate shaping of the lead for better insertion of the lead into a blood vessel, for advancing electrode 12 into contact with the heart or any other desired location. Stylet 20 is typically removed after proper placement of pacing lead 10.

Figures 1, 2, 3, 4:
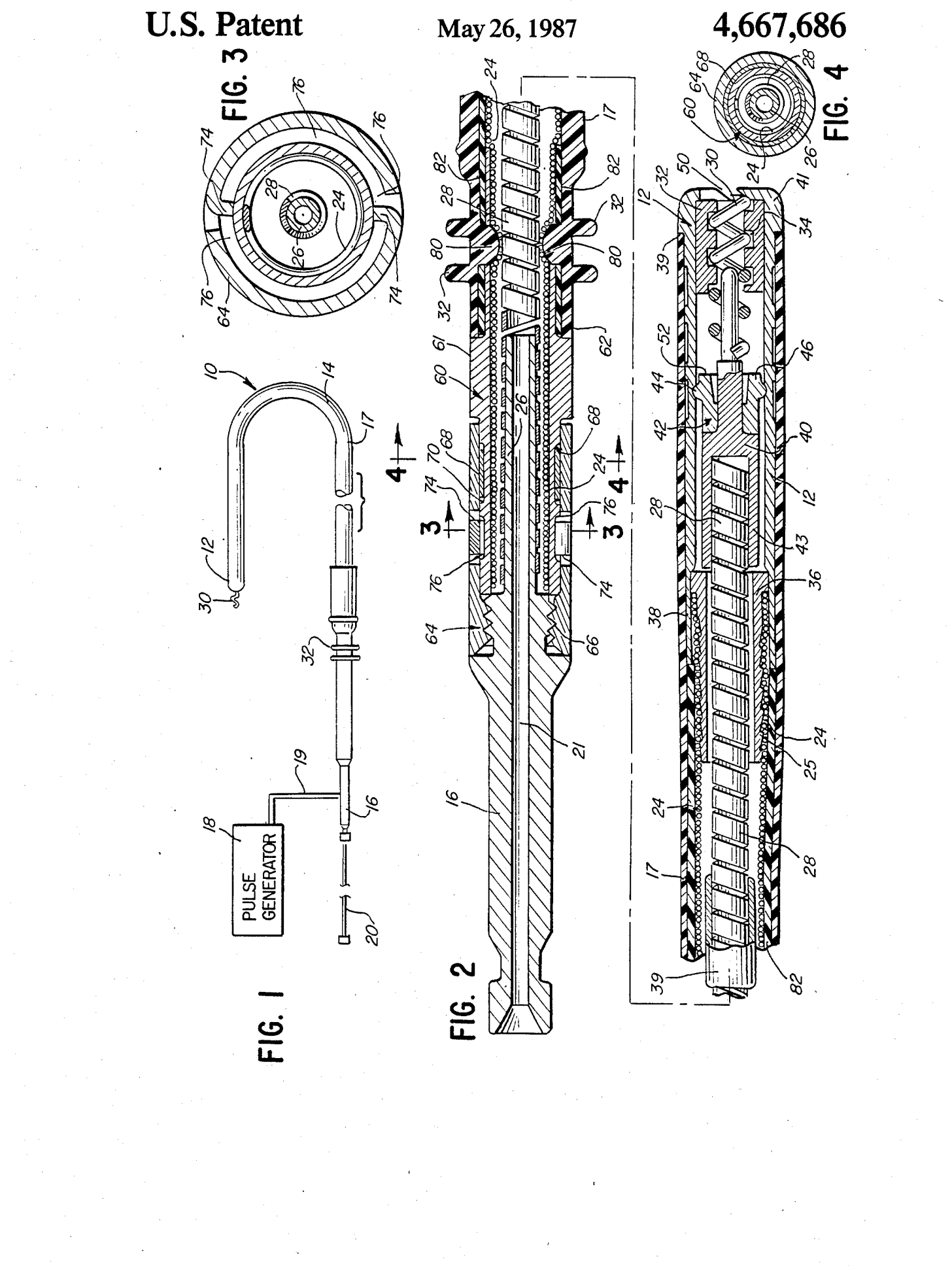

Terminal assembly 16 defines a forwardly positioned sleeve 26 to which a helical ribbon 28 of stainless steel is secured to function as the driver coil. Driver coil 28 is secured at its other end to fixation means 30, which is shown to be a helical rod of stainless steel with a pointed end. Accordingly, as terminal assembly 16 is rotated, rotational torque is transmitted through driver coil 28 to fixation means 30, to advance means 30 forwardly from the position shown in FIG. 2 to the position shown in FIG. 1. Typically the helical pin or rod 30 serving as the fixation means will embed itself in the muscle of the heart wall during this operation to secure electrode 12 into the desired position for imparting electrical pulses to the desired section of heart muscle.

Turning first to details of the distal end of pacing lead 10, tubular electrode 12 is shown to surround insulating plastic tubular member 32, which defines a helical groove 34 through its inner bore through which the helical pin 30 moves as it is rotated. Inner sleeve 36 is provided, being typically made of non-conductive material, to press the end of coil of conductor wire 24 against the inner surface of the tubular shank 38 of electrode 12, to provide good electrical contact therebetween. Wire coil 24 may be sealed to inner sleeve 36, and annular serrations 25 may be provided in inner sleeve 36 to facilitate this.

Sleeve 39 of radioopaque material may be carried on coil 28 to provide X-ray visualization of lead 10.

Electrode 12 may be made of porous, sintered metal. Alternatively, electrode 12 may be made of sintered metal at its outermost end, but the remainder of the tubular electrode may be of the same material of non-porous nature. Suitable materials for electrode 12 include platinum-iridium alloys, platinum, or certain known alloys of cobalt.

It can be seen that sheath 17 encloses most of electrode 12 but exposes the distal end 41. Electrode 12 carries annular ledge 39 to receive outer sheath 17 in smooth manner, so that typically one or two mm. of electrode 12 are laterally exposed as distal end 41.

Helical pin 30 is carried on shaft 40 which, in turn, defines sleeve 43, which receives and is bonded to driver coil 28. Shaft 40 may be manufactured of a rigid, non-conductive material such as polyethersulfone.

Sealing skirt 42 is a tubular structure which is preferably made of silicone rubber. Skirt 42 defines an external annular rib 44 on skirt portion 46, which is biased into sealing contact with the inner wall of tubular shank 38 of electrode 12. It can be seen that annular rib 44 is the only part of sealing skirt 42 which is in contact with sleeve 12. Sealing skirt 42 may be bonded by appropriate adhesive to shaft 40.

Accordingly, as drive coil 28 is rotated by the rotational action of terminal pin 16, it rotates sealing skirt 42, which in turn rotates shaft 40 and helical pin 30, typically to rotationally advance helical pin 30 forward from the position of FIG. 2 to the position of FIG. 1. Body fluids seeping to the interior of electrode 12 through aperture 50 are prevented from free migration throughout the interior of lead 10 by the sealing action of sealing skirt 42. In the advanced position of helical pin 30, sealing skirt 42 will have advanced to a position closely adjacent to or in contact with member 32, and if sufficiently advanced, forward edge 52 of sealing skirt 42 can enter into sealing contact with the facing end of tubular member 32 for additional sealing.

The presence of shaft 40 facilitates the alignment of the system, reducing frictional forces tending to increase the torque required to rotate helical pin 30 for advancement thereof.

In may be desired to coat helical pin 30 with graphite, making use of a conventional process, to reduce the torque required in rotating helical pin through tubular member 32. The interior of tubular member 32 may be alternatively or also coated with graphite, as may be desired.

Turning now to the proximal end of lead 10, the proximal end of helical electric wire 24 is electrically connected to first sleeve 60, which is made of electrically conductive metal. First sleeve 60 is generally stationary, and does not rotate upon rotation of terminal pin 16 and driver coil 28 in the manner described above. Sleeve 60 also is sealed to the proximal end 62 of outer casing 17 of the fixation lead of this invention. A portion 61 of sleeve 60 may be exposed to the exterior to serve as an auxiliary terminal.

A second sleeve 64, made of conductive metal, also is provided, being in intimate, electrically conductive, screw threaded contact with terminal pin 16 by means of screw threads 66 and also by spot welding, if desired. Both sleeves 60 and 64 may be made of stainless steel, for example.

To facilitate electrical contact between sleeves 60 and 64, a strip of conductive metal 68, particularly a springy gold nickel alloy, is placed in annular groove 70 in such a manner that strip 68 is deformed from its normal, flat configuration into a "C" shape within groove 70. Gold strip 68 may actually be of a length to assume practically an O-shape, although the ends of the strip should be separate from each other. Strip 68 should be thick enough to have a springing, resilient action urging back to a flat configuration, or at least some other configuration than the "O" or "C" shape into which it is forced within groove 70. Groove 70 may have a depth of about 0.005 inch while the thickness of gold strip 68 may be about 0.004 inch, by way of example and not limitation. In this circumstance, the springing resistance of strip 68 to being forced into the shape it must assume within groove 68 causes the ends of the strip to stay in firm contact with second sleeve 64, while central portions of the sleeve are in contact with first sleeve 60. Thus, strip 68 is in intimate contact with the inner wall of sleeve 64 and the outer wall of sleeve 60 at all times, even after sleeve 64 engages in rotation relative to sleeve 60 during the process of advancing or retracting helical pin 30. Accordingly, a reliable electrically conductive path is provided, despite the relatively movable relationship of sleeves 60 and 64, so that electrical pulses from pulse generator 18 can pass via conductor 19 to terminal pin 16, and then sequentially to second sleeve 64, gold strip 68, first sleeve 60, conductor coil 24, and then to tubular sleeve 12 which serves as the electrode, for conveying pulses of electrical current to a selected portion of the heart.

As an alternate securing mechanism, driver coil 28 may fit into a recess in terminal pin 16 rather than being carried on sleeve 26.

Tabs 74, carried by second sleeve 64, are provided to fit into second annular groove 76 of first sleeve 60. As the result of this, sleeves 60 and 64 can rotate relative to each other, but cannot be separated, since significant longitudinal motion is prevented by the tabs 74 which occupy annular groove 76.

First sleeve 60 defines one or more apertures 80. The material of silicone outer sheath 17, which may be molded onto the lead, extends into apertures 80 to increase the resistance of the lead against separation of the various parts on longitudinal pulling.

Inner insulation coating 82 may also be provided along the majority of the length of lead 10, upon which the silicone sheath is molded or otherwise applied.

The above has been offered for illustrative purposes only, and is not intended to limit the scope of the invention of this application, which is as defined in the claims below.

That which is claimed is:

1. In an active fixation lead which defines a central bore and comprises a length of insulated electrical wire having a rotatable terminal pin at a proximal end thereof; means for enabling rotation of the terminal pin; driver coil means connected to said terminal pin and extending through said bore to a distal end of said lead; and fixation means carried at the distal end of said lead having an affixing position and a retracted, non-affixing positon, said fixation means being connected to said driver coil means and movable between said positions by rotation of said terminal pin, an electrical contact at the distal end of the lead, the improvement comprising, in combination:

a first conductive metal sleeve adjacent said proximal end of the lead, said first sleeve being electrically connected to said electrical wire; a second conductive metal sleeve carried by said terminal pin, said first and second sleeves being in telescoping relation with one of the sleeves being located within the other sleeve and with the second sleeve being rotatable relative to said first sleeve; said first and second sleeves defining an annular slot which extends longitudinally between them; and a conductive metal spring strip positioned between said first and second sleeves within said slot; said spring strip having a substantial width extending longitudinally within said slot to contact a substantial portion of said first and second sleeves, said spring strip being biased outwardly so that the strip presses against both the first and second conductive sleeves by spring action, whereby improved electrical contact is provided between said terminal pin and electrical wire; and interconnecting means for preventing disconnection of said first and second sleeves from their telescoping relation.

2. The active fixation lead of claim 1, in which said conductive metal spring strip comprises gold.

3. The active fixation lead of claim 1 including means connecting said second conductive metal sleeve to said terminal pin in screw-threaded relation.

4. In an active fixation lead which defines a central bore and comprises a length of insulated electrical wire having a rotatable terminal pin at a proximal end thereof, means for enabling rotation of the terminal pin, driver coil means connected to said terminal pin and extending through said bore to a distal end of said lead, and fixation means carried at the distal end of said lead having an affixing position and a retracted, non-affixing position, said fixation means being connected to said driver coil means and movable between said positions by rotation of said terminal pin, an electrical contact at the distal end of the lead, the improvement comprising, in combination:

a first conductive metal sleeve adjacent said proximal end of the lead, said first sleeve being electrically connected to said electrical wire;

a second conductive metal sleeve carried by said terminal pin, said first and second sleeves being in telescoping relation with one of the sleeves being located within the other sleeve and with the second sleeve being rotatable relative to the first sleeve; said first and second sleeves defining an annular slot which extends longitudinally between them;

a conductive metal spring strip positioned between said first and second sleeves within said slot, said spring strip having a substantial width extending longitudinally within said slot to contact a substantial portion of said first and second sleeves, said spring strip being biased outwardly so that the strip presses against both the first and second conductive sleeves by spring action, said second sleeve carrying a portion of the first sleeve in its bore, said second sleeve defining inwardly projecting tab means, and the first sleeve defining an outwardly facing annular slot positioned to receive said tab means to prevent disconnection of said sleeves from their telescoping relation, said electrical wire connecting at the end of said lead opposite to the first and second sleeves with a sleeve electrode positioned adjacent said fixation means, said fixation means comprising a helical pin carried on a shaft made of non-conductive plastic, said shaft being connected to said driver coil means, said shaft also being positioned within said sleeve electrode.

* * * * *